United States Patent [19]

Tustin et al.

[11] Patent Number: 5,413,681
[45] Date of Patent: May 9, 1995

[54] PROCESS FOR THE RECOVERY OF TEREPHTHALIC ACID AND ETHYLENE GLYCOL FROM POLY(ETHYLENE TEREPHTHALATE)

[75] Inventors: Gerald C. Tustin; Thomas M. Pell, Jr., both of Kingsport; David A. Jenkins, Gray; Mary T. Jernigan, Kingsport, all of Tenn.

[73] Assignee: Eastman Chemical Company, Kingsport, Tenn.

[21] Appl. No.: 151,637

[22] Filed: Nov. 15, 1993

[51] Int. Cl.$^6$ .............................................. B01D 3/00
[52] U.S. Cl. ............................ 203/80; 203/DIG. 11; 203/DIG. 16; 560/78; 560/79; 568/868; 568/871
[58] Field of Search ........ 203/80, DIG. 16, DIG. 11, 203/49, 79; 568/868, 871; 560/78, 79; 562/485; 34/19; 210/770, 787

[56] References Cited

U.S. PATENT DOCUMENTS

| | | | |
|---|---|---|---|
| 3,330,863 | 7/1967 | Read et al. | 546/223 |
| 3,362,989 | 1/1968 | McMakin et al. | 562/485 |
| 3,367,847 | 2/1968 | Pierson | 203/41 |
| 3,522,298 | 7/1970 | Bryant et al. | 562/487 |
| 3,637,831 | 1/1972 | Remsberg | 562/487 |
| 3,703,488 | 11/1972 | Morton | 521/48.5 |
| 4,225,394 | 9/1980 | Cox et al. | 203/71 |
| 4,355,175 | 10/1982 | Pusztaszeri | 562/483 |
| 4,578,502 | 3/1986 | Cudmore | 560/79 |
| 4,578,510 | 3/1986 | Doerr | 562/483 |
| 4,605,762 | 8/1986 | Mandoki | 562/483 |
| 4,620,032 | 10/1986 | Doerr | 562/483 |
| 5,045,122 | 9/1991 | Tindall et al. | 134/29 |
| 5,095,145 | 3/1992 | Rosen | 562/483 |
| 5,101,064 | 3/1992 | Dupoat et al. | 560/78 |

FOREIGN PATENT DOCUMENTS

| | | |
|---|---|---|
| 19 26 034.5 | 5/1969 | Germany . |
| 49-41329 | 4/1974 | Japan . |
| 1107994 | 3/1968 | United Kingdom . |

OTHER PUBLICATIONS

The Kinetics of High–Temperature Hydrolytic Depolymerization of Poly(Ethylene Terephthalte), *Antec '92*, by J. R. Campanelli, M. R. Kamal, and D. G. Cooper; pp. 270–273.

Mobil's Process for TPA, *Chemical Engineering Progress*, 9/71, vol. 67, No. 9, by H. S. Bryant, C. A. Duval, L. E. McMakin, & J. I. Savoca; pp. 69–75.

*Primary Examiner*—Virginia Manoharan
*Attorney, Agent, or Firm*—Bernard J. Graves, Jr.; Harry J. Gwinnell

[57] ABSTRACT

A process useful for the recovery of terephthalic acid and ethylene glycol from poly(ethylene terephthalate) or its copolymers. The process is economical, beneficial to the environment and provides polymer grade terephthalic acid and ethylene glycol from post-consumer resin. The process is a six-step process including: (1) contacting a resin containing poly(ethylene terephthalate) with water at elevated temperature and pressure, (2) cooling the resulting mixture to provide a solid portion containing terephthalic acid and a liquid portion containing ethylene glycol, (3) recovery of the ethylene glycol from the liquid portion by distillation, (4) recovery of the terephthalic acid by heating the solid portion in the presence of water vapor at elevated temperature to produce a vapor containing terephthalic acid and water, (5) cooling terephthalic acid water vapor mixture to a temperature below the dew point of terephthalic acid and (6) collecting the polymer grade terephthalic acid. The polymer grade terephthalic acid and ethylene glycol provided by this process can be used to make high quality terephthalate homopolymers or copolymers for applications including clear bottles and fibers.

23 Claims, No Drawings

PROCESS FOR THE RECOVERY OF TEREPHTHALIC ACID AND ETHYLENE GLYCOL FROM POLY(ETHYLENE TEREPHTHALATE)

FIELD OF THE INVENTION

This invention relates to a process for the recovery of terephthalic acid and ethylene glycol from poly(ethylene terephthalate) via a neutral hydrolysis process, followed by various purification steps.

BACKGROUND OF THE INVENTION

Poly(ethylene terephthalate) (PET) is a large volume resin finding application in the production of fibers, molded articles and packaging materials. Soft drink beverage bottles are made from resins comprised mainly of PET. Discarded beverage bottles do not degrade at acceptable rates by natural processes in the environment, and hence present both a litter and a disposal problem. One desirable way to lessen the amount of PET bottle refuse in the environment is to recycle the polymer into new PET bottles. Because of fortuitous contact of some post-consumer bottles with harmful substances, such as pesticides, a successful recycling technique will almost certainly mandate that the polymer be depolymerized to purified monomers.

A successful depolymerization process must be able to remove other substances that may be present in the resin such as isophthalic acid (IPA) and 1,4-cyclo-hexanedimethanol (used to control crystallinity), dyes and pigment (used to color certain bottles) and polymerization catalyst metals. Much of the PET produced is prepared from polymer grade terephthalic acid (PTA) rather than dimethyl terephthalate (DMT), and thus a suitable recycling process should produce PTA for processes that use it as a starting material.

U.S. Pat. No. 5,045,122 describes a saponification process for the degradation of PET into salts of terephthalic acid (TPA). A similar procedure that produces salts of TPA is described in U.S. Pat. No. 4,355,175, but the polymer is first dissolved in concentrated sulfuric acid—a step which generally has a detrimental effect on the ethylene glycol (EG) portion of the resin. Both of these references describe recovery of the terephthalic acid by neutralization of the salts with acid. Both of these processes are wasteful because acid and base are consumed and salts are created. Disposal of the salts thus has a negative effect on the environment. Accordingly, a need exists for an economical process for the recovery of both EG and TPA from PET in a manner that will not harm the environment.

U.S. Pat. No. 3,703,488 describes a method for degrading PET by mixing with TPA or ethylene glycol at elevated temperature. The resulting partially depolymerized material is then incorporated in the preparation of new resin. PTA is not produced by this method, and no means is provided to remove typical contaminants such as polymerization metal catalysts, dyes, pigments, other glycols and dicarboxylic acids, or fortuitous contaminants such as insecticides and gasoline.

U.S. Pat. No. 4,620,032 describes a related glycolysis process wherein the resin is partly depolymerized with EG and then hydrolyzed at elevated temperature and pressure, thus allowing for a shorter hydrolysis time compared to that required for resin not treated with EG. This method does not provide for the removal of contaminants such as polymerization metal catalysts, dyes, pigments, other glycols and dicarboxylic acids.

U.S. Pat. No. 5,101,064 describes a related process whereby the resin is treated with an excess of an alcohol having 6–20 carbon atoms, and ethylene glycol can be distilled from the mixture. Because transesterification is an equilibrium process, a large excess of the alcohol is generally required to obtain an acceptable yield of diesters of TPA (even though distillation of ethylene glycol favors the formation of the ester of the reactant alcohol because of the equilibrium), and, in order to obtain PTA, subsequent purification and hydrolysis steps would be required. A large alcohol recycle stream would be generated by such a process. Discharge of the alcohol or its by-products to the environment must be avoided, and this requirement makes this process relatively complicated and uneconomical.

DE 1,926,034 describes a process whereby PET is contacted with tall oil fatty acid at elevated temperature. Although this technique does not require a pressure vessel, it is also an equilibrium controlled process. Thus, a large excess of the fatty acid is required if an acceptable yield of TPA is to be obtained, and a large tall oil fatty acid recycle stream would be generated. Also, the process generates tall oil fatty acid esters of ethylene glycol. Thus, additional hydrolysis and purification steps would be required to recover the ethylene glycol. Discharge of the tall oil fatty acid or its by-products to the environment must be avoided, and this requirement makes this process relatively complicated and uneconomical. The process does not remove pigment colorants and other contaminants. Thus, a need exists for a process for the recovery of both PTA and EG from PET that will remove polymerization metal catalysts, dyes, pigments, fortuitous contaminants such as insecticides and gasoline, other glycols and dicarboxylic acids and that will not require the use of large volumes of environmentally undesirable reagents.

U.S. Pat. No. 4,578,502 describes an elevated temperature (about 177°–288° C.) and pressure (about 350–1500 psig) neutral hydrolysis process for the recovery of monomers from scrap PET. Related processes are described in U.S. Pat. No. 4,578,510 and U.S. Pat. No. 4,605,762. An attractive feature of these processes is that the ethylene glycol is easily recovered from relatively concentrated aqueous solutions by distillation.

U.S. Pat. No. 5,095,145 emphasizes that these type of neutral hydrolyses at elevated temperatures and pressures provide crude TPA that is unsuited for use as a monomer for PET. Further purification is accomplished by reslurrying the crude TPA in water and hydrogenating at elevated temperature and pressure in the presence of a noble metal catalyst. This treatment improves the color of the TPA, but the material still contains up to 100 ppm metals. None of these neutral hydrolysis techniques efficiently remove isophthalic acid, pigments, polymerization metal catalysts and fortuitous contaminants to the degree required for the production of PTA suitable for the use as a monomer for the production of PET. Complete hydrolysis is difficult to achieve.

Although some improvement in product quality might result from repeatedly redissolving the TPA at elevated temperature in water, filtering, cooling, recovering and washing the solid, many such steps would be required to achieve only a marginal improvement, and the process would thus be uneconomical. The difficulty arises from the similar solubility characteristics of many of the species present (such as IPA) to those of TPA and from the submicron size of many of the pigment particles which makes effective filtration difficult. The production of a uniform quality PTA from recycled polymer of varying composition would be difficult with processes based upon continuous neutral hydrolysis process. Thus, although neutral hydrolysis is an efficient way to produce crude TPA and readily recoverable ethylene glycol, a there is a need for the production of PTA of uniform high quality substantially free of IPA, pigments, fortuitous contaminants and polymerization metal catalysts.

Japanese Kokai Patent Application No. SHO 49[1974]-41329 describe the degradation of PET by superheated steam at 300°–400° C. at near ambient pressure. In this technique, TPA is vaporized as the polymer degrades and is collected by cooling the vapor stream. Since the TPA is produced in solution in the liquid melt before vaporization, the process is actually a distillation rather than a sublimation (sublimation is the passage from a solid state to a vapor state).

Other species vaporize along with the TPA, and these include 2-hydroxyethyl terephthalic acid (HETA), bis(2-hydroxyethyl) terephthalate (BHET), oligomers, ethylene glycol and ethylene glycol decomposition products. The formation of ethylene glycol decomposition products is expected when the polyester is pyrolyzed at temperatures in excess of 300° C. as described in the literature (See, for example, March, J. *Advanced Organic Chemistry: Reactions, Mechanisms, and Structure;* McGraw-Hill, Inc.: New York, 1968; pp 756–757.).

A certain amount of decarboxylation occurs in the described process, although the extent is less when steam is present than when it is omitted. In addition to low observed conversions, the purity of the TPA produced by this method is typically only in the region of 70–80%. Acceptable TPA is obtained only after solvent washing and recrystalliztion using acetic acid. Thus this process is not only inefficient, but additional purification steps are required to provide pure TPA. Thus, a need still exists to provide for the efficient high yield production of polymer grade TPA and EG.

U.S. Pat. No. 3,330,863 describes a steam sublimation process for the purification of crude TPA produced from the oxidation of p-xylene. Related disclosures are British Nos. 1,163,665, 1,110,649 and 1,107,994, Belgian No. 719,187 and U.S. Pat. No. 3,362,989. A review article has been published (Bryant, H. S.; Duval, C. A.; McMakin, L. E.; Savoca, J. I. Chem. Eng. Progress 1971, 67, 69–75.). The primary impurity removed by this process is 4-carboxybenzaldehyde, and in some cases the process is performed in the presence of hydrogen gas and a noble metal catalyst to convert this impurity to 4-toluic acid. All of the processes involve heating the crude terephthalic acid in the presence of steam to a temperature sufficiently high to vaporize most of the TPA (about 315° C.), filtration of the vapor phase to remove nonvolatile entrained solids and cooling to below the dew point of TPA. Steam is necessary to prevent anhydride formation.

The crude solid TPA is entrained in the vapor stream before it is vaporized. Crystallization is induced by contacting the hot vapor stream with cold TPA, liquid (generally water) or both, and generally the product is collected in cyclone separators or in filters. The steam sublimation process has never been demonstrated for the purification of crude TPA produced from post-consumer PET such as in the neutral hydrolysis with liquid water at elevated pressure.

Further, the teachings of Japanese Kokai Patent Application No. SHO 49[1974]-41329 suggest that undesirable degradation processes might occur because the crude product contains unhydrolyzed esters. Thus, a need exists to demonstrate that crude product derived from post-consumer or recycled PET such as the neutral hydrolysis of PET at elevated temperature and pressure can be converted in high yield to PTA, substantially free of HETA, BHET, oligomers, polymerization metal catalysts, IPA, dyes, pigments and fortuitous contaminants by a steam sublimation process.

The object of the present invention is to provide a process which converts poly(ethylene terephthalate) and its copolymers, including post-consumer products containing poly(ethylene terephthalate), into ethylene glycol and terephthalic acid. A further object of the invention is to provide ethylene glycol and terephthalic acid that is sufficiently pure to be suitable for the preparation of high quality high molecular weight poly(ethylene terephthalate) polymer suitable for use in clear bottles, fibers, etc., and that is substantially free of pesticide residues, gasoline residues, partially hydrolyzed esters, other glycols, other dicarboxylic acids, polymerization metal catalysts, dyes, pigments, and other fortuitous contaminants. A further object of the invention is to provide ethylene glycol and terephthalic acid in an economical manner without the use or production of organic reagents, products or inorganic salts and, therefore, in a manner that is safe and that has a minimal effect on the environment.

SUMMARY OF THE INVENTION

This invention provides a process useful for the recovery of terephthalic acid and ethylene glycol from poly(ethylene terephthalate). The process is economical, safe, beneficial to the environment and provides polymer grade terephthalic acid and ethylene glyol from post-consumer resin.

The invention is a six-step process comprising: (1) contacting a resin containing poly(ethylene terephthalate) with water at elevated temperature and pressure, (2) cooling the resulting mixture to provide a solid portion containing terephthalic acid and a liquid portion containing ethylene glycol, (3) recovery of the ethylene glycol from the liquid portion by distillation, (4) recovery of the terephthalic acid by heating the solid portion in the presence of water vapor at elevated temperature to produce a vapor containing terephthalic acid and water, (5) cooling terephthalic acid water vapor mixture to a temperature below the dew point of terephthalic acid and (6) collecting the polymer grade terephthalic acid. The polymer grade terephthalic acid and ethylene glycol can be used to make high quality terephthalate homopolymers or copolymers for applications including fibers and clear bottles.

DETAILED DESCRIPTION OF THE INVENTION

The present invention provides a process for the recovery of ethylene glycol and terephthalic acid from a resin comprised of poly(ethylene terephthalate), the process comprising the steps:

(a) contacting the resin with water at a range of about 200° C. to 280° C. in a reaction vessel at the vapor pressure of water at said range to form a mixture comprised of about 1 to 40 weight percent of the resin;

(b) cooling the mixture with water at about 70° C. to 100° C., filtering the solids, washing the solids and then drying the solids at a temperature of from about 25° C. to 100° C. to provide a solid portion comprised of the terephthalic acid and a liquid portion comprised of ethylene glycol;

(c) recovering the ethylene glycol from the liquid portion of the mixture by a two-step distillation, wherein in a first step of the two-step distillation the water and low boiling components are removed at about 0.1 to 6 atmospheres pressure and temperatures of about 100° C. to 170° C., and wherein in a second step of the two-step distillation high boiling species are removed at about 1 mm Hg to 10 atmospheres pressure and at a temperature range of about 50° C. to 300° C.;

(d) recovering the solid terephthalic acid by heating the solid portion above its dew point with a continuous stream of water vapor at a temperature of about 310° C. to 370° C. and a pressure of about 0.1 atmosphere to 1.2 atmosphere to produce a vapor comprised of the water and terephthalic acid;

(e) cooling the vapor containing the terephthalic acid and the water to a temperature below the dew point of the terephthalic acid and;

(f) collecting the solid polymer grade terephthalic acid.

As noted above, the present invention provides a process for the recovery of ethylene glycol and terephthalic acid from a resin comprised of poly(ethylene terephthalate) (PET) and its copolymers. It should be appreciated that the term "PET" refers to polyesters comprised of ethylene glycol and terephthalic acid residues, optionally modified with other monomers. In a preferred embodiment of the process, the PET is comprised of greater than 50 percent by weight of terephthalic acid residues. In a further preferred embodiment, the PET is modified with less than 10 mole percent of 1,4-cyclohexanedimethanol, other glycols, isophthalic acid, and other dicarboxylic acid modifiers. The crude substrate, i.e., the resin, or resin blend may also be contaminated with up to about 20 weight percent of other resinous species such as polyolefins, polyvinyl chloride, polycarbonates, polyurethanes, and the like.

The process comprises the steps of initially contacting the resin with water at a temperature range of about 200° C. to 280° C. in a reaction vessel at the vapor pressure of water at such a temperature range to provide a mixture comprised of about 1 to 40 weight percent of the resin in water. The residence time of the resin in the reaction vessel will vary according to the temperature of the reaction vessel and the concentration of the resin. The preferred time is 0.5 to 5 hours and the most preferred time is 0.5 to 3 hours.

Next, the mixture is cooled to about 25° C. to 100° C., the solids formed therefrom are filtered, the solids are washed with, for example water, and then dried at a temperature from about 70° C. to 100° C. to provide a solid portion comprised of the terephthalic acid and a liquid portion comprised of the ethylene glycol.

Recovery of the ethylene glycol from the liquid portion of the mixture may be accomplished by a two-step distillation. In the first step of the two-step distillation, water and low boiling species are removed at about 0.1 to 6 atmospheres pressure and temperatures of about 100° C. to 170° C. and in a second step of the two-step distillation high boiling species are removed at about 1 mm Hg to 10 atmospheres pressure and at a temperature range of about 50° C. to 300° C.

Next, recovery of solid terephthalic acid can be accomplished by heating the solid portion comprising terephthalic acid from step (b) to its dew point with a continuous stream of water vapor, the water vapor heated to a temperature of about 310° C. to 370° C. and a pressure of about 0.1 atmosphere to 1.2 atmosphere, to provide a vapor comprised of the water and terephthalic acid.

Finally, the vapor is cooled to a temperature below the dew point of the terephthalic acid and the solid polymer grade terephthalic acid formed therefrom is collected.

As a further aspect of the present invention, there is provided a process for the recovery of ethylene glycol from a resin comprised of poly(ethylene terephthalate). The process comprises practice of steps (a) through (c) above.

As a further aspect of the present invention, there is provided a process for the recovery of polymer grade terephthalic acid from a resin comprised of poly(ethylene terephthalate) after depolymerization of the poly(ethylene terephthalate), the process comprising the steps:

(d) recovering solid terephthalic acid by heating solid crude terephthalic acid above its dew point with a continuous stream of water vapor at a temperature of about 310° C. to 370° C. and a pressure of about 0.1 atmosphere to 1.2 atmosphere to produce a vapor comprised of the water and the terephthalic acid;

(e) cooling the vapor containing the terephthalic acid and the water to a temperature below the dew point of the terephthalic acid and;

(f) collecting the polymer grade terephthalic acid formed therefrom; wherein the solid crude terephthalic acid in step (d) is prepared by depolymerization of a resin comprised of poly(ethylene terephthalate).

Thus, it should be appreciated that the present invention provides a process for the neutral hydrolysis of poly(ethylene terephthalate) and the purification of its major constituent monomers, as well as methods for the isolation of either ethylene glycol or terephthalic acid. It should also be appreciated that the processes for monomer purification described in this invention could be used in conjunction with other depolymerization methodologies, for example, basic or acidic hydrolysis, acidolysis, glycolysis/hydrolysis, and the like.

The process of the present invention is suitable for PET from a variety of sources and in forms where it has been mixed with other materials. Pre-consumer resin and post-consumer resin such as fibers, molded articles and packaging materials (including beverage bottles) are satisfactory sources. The resin may contain other additional components added during the original polymerization process such as copolymerized 1,4-cyclohexanedimethanol, other glycols, isophthalic acid, other dicarboxylic acids, monomer decomposition byproducts, polymerization catalysts, stabilizers, dyes and pigments. Generally the preferred sum of these components added during the polymerization process should be less than 10 wt. %. Higher amounts can be tolerated, but additional purification steps may be required.

Often, any additional purification steps that may be required are merely repetitions of one or more steps of the claimed invention. Other resins, such as polyethylene, polypropylene, poly(vinyl chloride) and polystyrene may be physically mixed with the PET. Additional purification steps may be necessary if significant quantities (about 5 wt. % or more) of other condensation polymers, such as polyurethanes, polyamides or other polyesters are present.

Other bulk materials, such as glass, aluminum, iron, other metals, wood, paper and cotton may be physically mixed with the PET. Common consumer organic chemicals, such as lindane, paint thinner and gasoline may be present as contaminants. In a preferred embodiment, the source of the starting material is PET recovered from a common high volume use, such as soft drink bottles. Optional steps, such as removal of accompanying bulk solids and cleansing of soft drink bottles, may make the practice of the process of the invention more facile.

The process of the invention will depolymerize PET objects of a wide variety of shapes and sizes. It is preferred that the PET be granulated or shredded before it is conveyed to the hydrolysis reactor. The PET may then be conveyed to the hydrolysis reactor by extrusion, as a pumpable slurry in water, gas entrainment, gravity feed or similar method. The amount of water is preferably such that the resin will comprise about 5 to 40 wt % of the hydrolysis mixture. A more preferred mixture will contain about 10 to 30 wt % resin. The most preferred mixture contains about 15 to 25 wt % resin.

Mixtures with high amounts of resin tend to give incomplete hydrolysis due to equilibrium limitations. Those with low amounts of resin tend to give aqueous solutions that are dilute in ethylene glycol thus making its recovery less economical. The mixture can be heated under pressure, preferably with some form of stirring or agitation, to a temperature ranging from about 180° C. to about 300° C. A more preferred temperature range is from about 200° C. to about 260° C. The most preferred range is from about 215° C. to about 230° C.

Lower temperatures generally cause slow hydrolysis rates and can give incomplete reaction over reasonable time periods. Higher temperatures cause undesired decomposition reactions of the ethylene glycol component liberated from the resin. The neutral hydrolysis process pressure range from about 350 psig to about 1500 psig. In a preferred embodiment, an inert gas such as nitrogen or argon is also present to prevent degradation due to the action of oxygen on the resin or its hydrolysis products.

Residence times in the neutral hydrolysis reactor range from about 0.5 to 5 hours with 0.5 to 3 hours being satisfactory in most cases. Depending on the types of contaminants present with the PET, bulk solids may be separated after the neutral hydrolysis by gravity, hydrocycloning or other means. Fine solids may be largely removed by filtration of the pressurized hot mixture. Other resins, such as polyolefins, in their molten state may be largely removed by skimming or by decantation depending on their density. The neutral hydrolysis may be operated as a continuous, semicontinuous or a batch process.

In step (b) of the process of the invention the hydrolysis mixture is cooled and the pressure is released. This process may optionally be performed as a flash crystallization whereby the release of pressure on the hot mixture causes vaporization of a portion of the liquid component containing water and ethylene glycol, and substantial cooling of the remaining mixture and crystallization. The crude TPA is collected by filtration or centrifugation. If the mixture is cooled and filtered under pressure, the temperature of the mixture should be less than about 150° C. If the mixture is flashed before filtration, the temperature should be less than about 90° C. during the filtration.

In a preferred embodiment, the crystals are washed with water (preferably at 70° C. to 100° C.) to further remove water-soluble impurities, then dried (from about 25° C. to about 100° C.) to remove volatile impurities. In those cases where the starting resin is very contaminated, it may be desirable to repeat the neutral hydrolysis crystallization steps one or more additional times.

Step (c) of the process of the invention is the recovery of the ethylene glycol. The preferred method of recovery is a two-step distillation. The first distillation separates the water and low boiling components such as acetaldehyde and 2-methyl-1,3-dioxolane from the higher boiling components, including ethylene glycol. This process can be accomplished at a pressure of about 0.1 to 6 atmospheres and temperatures from about 100° C. to about 170° C.

The second distillation step separates the ethylene glycol from nonvolatile or higher boiling species such as diethylene glycol, triethylene glycol, 1,4-cyclohexanedimethanol, and high boiling organic contaminants. This process is performed at about 1 mm Hg under high vacuum to about 10 atmospheres pressure and from about 50° C. to about 300° C. Additional refinements to the ethylene glycol recovery process may be required depending on the type of contaminants present. These can be made as required by those skilled in the art. The distillation may be practiced as either a continuous or a batch process.

Step (d) of process of the invention is sublimation of the solid produced in step (b) of the process. In this step the solid is heated to a temperature above its dew point. Sublimation will occur as long as conditions are such that the partial pressure of TPA in the vapor is less than the vapor pressure of the solid. If the pressures become equal, an equilibrium occurs, and the net transport of TPA from the solid to the vapor ceases. Thus sublimation will continue to proceed if some means is provided to remove the TPA from static vapor (such as condensing in an adjacent cooler region) or if the vapor stream is moving relative to the solid. Alternatively conditions can be chosen such that the volume of vapor is sufficiently high to allow all of the TPA to vaporize producing a vapor in which the partial pressure of TPA is less than the vapor pressure of solid TPA at the same temperature.

Because of the variety of techniques used to perform the sublimation, it is also possible to perform the sublimation over a considerable range of pressures and temperatures. The temperature of the dew point is lower at lower pressure. Suitable pressures range from about 0.0001 atmosphere to about 3 atmospheres. Suitable temperatures for the process range from above about 220° C. to less than about 400° C. for this pressure span, with the lower pressures used with the lower temperatures. An example of the low pressure-low temperature operation would be the molecular sublimation from a heated surface to an adjacent cold surface under high vacuum.

Mechanical and economic limitations tend to make the low pressure-low temperature operation impractical for large scale operation. A more preferred pressure region is from about 0.05 to 2 atmospheres. The most preferred pressure region is from about 0.1 to about 1.2 atmospheres. More preferred temperatures range from about 280° C. to about 390° C. The most preferred temperatures range from about 310° C. to about 370° C.

Because TPA tends to form anhydrides when heated, the sublimation is preferably conducted in the presence of a gas containing water. The gas should contain greater than about 5 mole % water and preferably greater than 30 mole % water. However, it can be essentially 100% steam prior to the vaporization of the major portion of the impure TPA obtained from the second step of the invention. The requirement of the presence of water becomes more important as the temperature is increased.

When the gas contains less than 100 percent steam, the balance is preferably other inert gases (such as nitrogen, argon, carbon dioxide, or certain combustion gases), organic acids (such as acetic acid), or ketones (such as acetone). Also, hydrocarbons (such as methane or xylenes) may be added. However, since an object of the invention is to have a safe process free from unnecessary and potentially hazardous reagents, the generally preferred sublimation medium is essentially 100 percent steam or steam plus an inert gas. Generally, it is not necessary to add a reducing gas such as hydrogen for the purpose of catalytic hydrogenation of impurities, but this does not have a detrimental effect on the process.

Typically the water-containing gas is moving. The solid may be held stationary in the presence of moving gas or, preferably, entrained in the moving gas. When the heated solid is held stationary in the moving gas at practical sublimation temperatures, the solid tends to sinter into a bulk mass. This reduces the efficiency of vaporization into the moving steam-containing gas. Thus, for large scale sublimation, the solid should be entrained in the moving water-containing gas at a temperature below the point where sintering occurs and then heated to above its dew point.

When the entraining gas is 100% steam at one atmosphere pressure, entrainment temperatures in the region of about 110° C. to about 160° C. are generally satisfactory. About 3 to 55 moles of steam per mole of TPA are generally required to completely vaporize the entrained TPA when it is subsequently heated to within the most preferred temperature region of about 310° C. to about 370° C. at between about 0.1 atmosphere and 1.2 atmosphere pressure with less steam being required at higher temperature. When moving gas is used to effect the sublimation, it is generally advantageous to pass the heated vapor stream through a filtration device to remove any nonvolatile solids still entrained in the gas before cooling the gas below the dew point of its components in step (e) of the invention. The sublimation can be performed in a batch or continuous manner.

The dew point varies as a function of the pressure, and mole ratio of water to TPA. For example, when the water:TPA ratio is 3:1 at about 0.1 atmosphere pressure then the dew point is 315° C. Accordingly, increasing the pressure to 1.2 atmospheres, with the same mole ratio, raises the dew point to 371° C. At the highest water:TPA mole ratio of 55:1 at 0.1 atmosphere the dew point is 267° C. The dew point is 312° C. under 1.2 atmospheres at the 55:1 ratio. It should be understood that the dew point values would be different if other diluents are present.

In step (e) of the process of the invention the heated vapor stream ensuing from step (d) is cooled to a temperature below its dew point. The condensation occurs when the partial pressure of the TPA in the vapor phase becomes equal or greater than the vapor pressure of the solid at the same temperature. As described above in step (d), this temperature is pressure dependent, and the same considerations apply. Generally, when the process is operated in the region of about 1 atmosphere pressure with the vapor stream nearly saturated with TPA at about 310° C. to 370° C., cooling the gas stream to about 280° C. or less effects condensation of most of the TPA. Lower pressures may require lower temperatures.

If the condensation temperature is in the region of about 260° C. to about 280° C. (at about 1 atmosphere) and the product is rapidly removed from the condensation zone, a very pure product can be obtained because species of higher volatility than TPA will not co-condense to the degree that they would at lower temperature. However, because TPA has a surface tackiness in this temperature range, mechanical difficulties are associated with removing it from the condensation zone. Although condensation at these temperatures is satisfactory for small scale sublimation, lower condensation temperatures are generally preferred for larger scale processes. Thus a condensation temperature below about 230° C. is preferred for large scale condensation of TPA from the vapor in the one atmosphere process.

Cooling can be effected by contacting the hot TPA-ladened vapor stream with a lower temperature solid, liquid or vapor or mixtures there of. In small scale desublimations the walls of the condensation vessel provide a suitable low temperature solid for the condensation. However the above-mentioned difficulties associated with tackiness and removal of the product from the condensation zone cause difficulties with large scale condensations. Recycled purified cold TPA can also be used to effect the desublimation.

Inert gas and steam at low temperature can also induce the condensation. Other low temperature vapors or liquids such as hydrocarbons, ketones, organic acids and the like are suitable. However, they are not preferred because of recycling requirements, potential safety hazards and possible environmental difficulties. For these same reasons along with its high heat of vaporization, liquid water is the preferred cool liquid used to induce the condensation. Generally it is preferable to contact the hot vapor with liquid water, with the contacting operation performed in such a manner so that the solids produced will not contact the wall portion of the vessel having a temperature of about 230° C. or less until the temperature of the solids is below that temperature as well.

When water is used as the cooling agent, the amount used depends on the original temperature of the TPA-ladened vapor and the desired final form and temperature of the refined TPA. If a large amount of liquid water were used and the final temperature were in the region of about 30° C. to about 100° C., the TPA would be in an aqueous slurry, and, although recovery would be high, the product may contain partly hydrolyzed esters and other condensable species. If sufficient water is added to initially cool the TPA-ladened vapor stream to temperatures in the region of about 210° C. to about 230° C., the TPA obtained will contain less impurities than that obtained at lower temperatures and will still be nontacky. If the condensation is done in this manner, additional quenching of the vapor stream ensuing from the collection zone associated with the 210° C.–230° C. condensation zone to temperatures in the region of about 30° C. to about 200° C. can provide additional solid condensate that is enriched in partly hydrolyzed esters.

In a preferred embodiment, a portion or all of this second condensate is recovered and returned to the neutral hydrolysis reactor for further conversion. The time required for the liquid water induced condensation typically ranges from about 0.1 seconds to about 100 seconds. The condensation process can be performed as either a batch or a continuous process. If necessary the sublimation/condensation processes can be repeated additional times until polymer grade TPA is produced upon recovery.

Step (f) of the invention is the collection of the purified TPA. The method of collection depends on the processes chosen for the sublimation/condensation. If the condensation is performed by contacting the hot TPA ladened-vapor with condenser vessel walls held at temperatures above about 230° C., mechanical methods, such as scraping, will be required. Accordingly, this method is best suited for small scale operation. This method is inconvenient for larger scale operations. Additional problems arise due to the insulating properties of the immobile condensate and possible decomposition reactions occurring when the TPA is held at high temperature for extended times. Thus some means of continuous condensation/recovery, such as a rotating condenser surface that is continuously scraped, would be required for large scale operation in this mode.

Similar difficulties will occur if the vessel condensation surface is held below about 230° C. Removal of the product from this surface will be somewhat easier due to the lower degree of sintering in the condensate. If the solid condensing surface is cold recycled purified TPA, the product can be collected by cycloning and/or filtration provided that contact with the vessel walls does not occur until the solid temperature is less than about 230° C. Otherwise, mechanical methods, such as scraping, will be required for some or all of the material.

Cycloning and filtration are the preferred means of collecting the products. These methods are used when the condensation is effected by contacting the hot TPA-ladened vapor with cold vapor or liquid provided material is not stuck to the condensation vessel walls. Mechanical methods, such as scraping, may be required if significant amounts of material adhere to the vessel walls. If the condensation is performed in portions to provide an enriched fraction at about 200° C. to about 230° C., the collection devices for that fraction should be kept at similar temperatures.

An additional collection device will be required for those systems producing two fractions of solid materials. If the collection device is held at temperatures of about 110° C. or higher, a dry product will be obtained when water is the entraining and/or condensing medium. A wet product can result if the collection vessel is below about 100° C. In this case an additional drying step may be required.

Preferably, one or more cyclones are used as the collection means. The collection devices are held at temperatures in excess of about 110° C. Once the product has been disengaged from the vapor stream and collection devices, it can be cooled or heated as desired. A portion or all of the water used in the sublimation/condensation operation can be returned to the neutral hydrolysis reactor or portions may also be returned to the sublimation/condensation operation. If further purification is required, the collected product can be returned for additional stages of sublimation/condensation. In some cases, the product can be purified further by digestion in acetic acid, although this is not a requirement of the invention. The collection process can be performed as a batch or continuous process.

The process of the invention may be logically extended, with some modifications known to those skilled in the art. Including, for example, recovering the components of other condensation polymers such as polyamides and other polyesters, especially those containing terephthalic acid.

The following examples are presented to illustrate the present invention, but are not intended in any way to limit the scope of the invention.

Experimental Section

EXAMPLE 1

This example illustrates the neutral hydrolysis portion of the invention and demonstrates that, although the hydrolysis is efficient, it does not provide polymer grade TPA when used alone. The PET used in this example was post-consumer uncolored bottle polymer that had been chopped into flakes. The PET had an inherent viscosity of 0.739 and contained 12 ppm Ti and 216 ppm Sb. The PET analyzed as containing 29.37 wt. % ethylene glycol, 1.77 wt. % diethylene glycol, 0.92 wt. % triethylene glycol, and 2.63 wt. % cyclohexanedimethanol.

The polymer (200 g) and distilled water (800 g) were charged into a stirred 1.8 liter Hastelloy C PARR ™ autoclave. The autoclave was pressurized with nitrogen to 250 psig, and the nitrogen pressure was released. The autoclave was repressurized with nitrogen to 250 psig, the stirrer was turned on, and the autoclave was heated to 220° C. The reaction was continued with stirring under autogenous pressure at 220° C. for 2 hours. The autoclave was then cooled to ambient temperature and vented. The mixture was removed from the autoclave and vacuum filtered.

The aqueous filtrate (670 g) was analyzed by high pressure liquid chromatography (HPLC), gas chromatography, X-ray florescence spectroscopy and atomic adsorption spectroscopy and contained the following species: 0.2 wt. % HETA, 0.023 wt. % acetaldehyde, 0.006 wt. % 2-methyl-1,3-dioxolane, 6.87 wt. % ethylene glycol, 0.43 wt. % diethylene glycol, 0.015 wt. % triethylene glycol, 0.121 wt. % cyclohexanedimethanol, 36 ppm Sb and 7 ppm Ni. BHET, TPA and Ti were not detected in the aqueous filtrate. The solids were washed with water and dried to yield an off white material (173 g). The solid was composed of 96.4 wt. % TPA and 2.4 wt. % HETA and contained 17 ppm Sb and 9 ppm Ti. The L*, a* and b* color characteristics of the solid were 92.5, −1.04 and 5.13 respectively.

EXAMPLE 2

This example illustrates that steam hydrolysis of PET as a sole technique is inefficient and destructive. The same source PET used in Example 1 was used in this example. The PET flake (19.2 g) was placed into a glass tube (1.5 inch O.D.×23.5 inches total length) having a tapered bottom and a steam inlet stem. Successive layers of quartz wool, quartz chips and quartz wool were placed above the PET sample as a filtration device, and the tube was positioned vertically in a three element electric furnace with the polymer sample in the center of the furnace and about half of the tube extending above the furnace.

The top portion of the tube was connected via a glass transfer line to a 500 ml 2-necked bottle fitted with a reflux condenser and provision for a positive pressure of nitrogen. A slight positive pressure of nitrogen was maintained throughout the duration of the reaction. The portion of the reactor outside of the furnace was heated with infrared lamps to prevent plugging by condensing materials. A stainless steel tube was attached to the steam inlet stem. Nitrogen gas was passed through the steam inlet stem and the furnace was heated to 220° C. The nitrogen was then shut off and steam preheated to 370° C. was fed through the steam inlet line at a rate of 0.68 g/minute while the furnace continued to heat up.

After the furnace temperature had reached 370° C., the steam feed was continued for 110 minutes. At this time a visual examination of the reactor revealed that the polymer had disappeared except for a brown film, and the reactor was allowed to cool. Solid products were isolated from the region of the reactor immediately above the furnace (4.81 g), the transfer line (4.66 grams) and the liquid condensate after filtration and drying (1.02 grams).

The beige colored solid from above the reactor contained 74 wt. % TPA, 8 wt % HETA, 0.47 wt % BHET with the balance being oligomeric and decomposition products. The solids from the transfer line contained 59.6 wt. % TPA, 8.3 wt. % HETA, 0.34 wt. % BHET with the balance being oligomeric and decomposition products. The solids from the liquid condensate contained 71.7 wt. % TPA, 17.1 wt % HETA, no detectable BHET with the balance being oligomeric and decomposition products. The liquid condensate (70.95 g) contained 0.28 wt. % HETA, 1.26 wt. % acetaldehyde 0.079 wt.% ethylene glycol and 0.004 wt. % diethylene glycol. Only 48% of the terephthalic acid and only 27% of the ethylene glycol could be accounted for in this example.

A similar reaction performed at 320° C. with 521.92 grams of water fed over 405 hours gave even poorer results with only 38% of the terephthalic acid and 22% of the ethylene glycol accounted for.

EXAMPLE 3

This example illustrates the process of the invention. It demonstrates that high purity TPA having excellent color containing essentially no polymerization metal catalysts, dyes or pigments can be obtained from green bottle polymer, and that the products can be obtained in high yield. In this particular example no deliberate attempt was made to control the condensation process other than to provide a cool surface.

The starting polyester for this example was 100% green bottle polymer manufactured by Eastman Chemical Company. The green bottle polymer was hydrolyzed as per Example 1. The light green solid isolated from the hydrolysis reaction contained 95.0 wt. % TPA, 4.3 wt. % HETA, 45 ppm Sb and 72 ppm Ti, and it had solution (KOH) color characteristics L*, a, and b* of 98.05, −2.76 and 7.53 respectively. Haze evident during the solution color measurements indicated presence of insoluble solids.

The apparatus of Example 2 was modified by removing the heat lamps and by wrapping the portion of the tube above the furnace and a portion of the transfer line with a loose spiral of electric heating tape. The heat tape was heated to about 320° C. throughout the sublimation process to allow for condensation to occur in the cooler regions between the spirals without plugging the vessel and transfer lines.

The sublimation tube was loaded with a portion of the above-described solids recovered from the hydrolysis of green bottle polymer (16.6 g). Successive layers of quartz wool, quartz chips and quartz wool were placed above the crude TPA sample as a filtration device. Nitrogen was passed through the steam inlet stem, and the furnace was heated to 220° C. The nitrogen was then shut off and steam preheated to 320° C. was fed through the steam inlet line at a rate of 0.21 g/minute while the furnace continued to heat up.

After the furnace had reached 320° C. the steam feed was continued for 396 minutes. The sublimation was monitored by periodic visual examination of the residual solid in the bottom of the tube. At the completion of the sublimation only a thin dark blue film remained in the base of the sublimation tube. The largest portion of product was a white solid (9.10 g) isolated from the region of the tube above the furnace heat zones.

This solid was analyzed by HPLC, and the analysis indicated that it was at least 95.7 wt. % TPA, and no HETA or BHET were detected. Analysis by gas chromatography indicated that the solid was 98.25 wt. % TPA. Antimony and titanium were not detected (detection limit was 1 ppm). Solution color measurements for this product gave L*, a, and b* values of 100.07, −0.53 and 0.53 respectively without observable haze. Additional solids were isolated from the heated portion of the transfer line (5.71 g) and the cold portion of the transfer line (wet with water: 4.38 g on a wet basis, 1.74 g on a dry basis). The liquid condensate (84.69 g) contained 0.036 wt. % ethylene glycol and 0.2 wt. % HETA. HETA was also detected in the solids isolated from the transfer lines. Based on the 15.77 g (95% of 16.6 grams) of TPA in the starting material and 15.05 grams of TPA found in the products, the accountability of the TPA was 96%.

EXAMPLE 4

This example illustrates the ability of the process of the invention to remove a common pesticide, lindane, from the PET. The example also demonstrates the ability to the sublimation/condensation process to provide polymer grade TPA free of partially hydrolyzed intermediates in one region of condensation while concentrating HETA and other impurities in other regions of condensation. The PET polymer sample used in this example is the same as used in Example 1. The polymer (100 g), lindane (0.1 g) and distilled water (300 g) were hydrolyzed at 220° C. and for 2 hours as per Example 1.

No lindane was detected in the wet solids nor in the filtrate from the hydrolysis reaction (detection limit by gas chromatography=20 ppb). The wet solids contained 10 ppm chlorine, and no chlorine was detected in the dry solids (detection limit=10 ppm). 98.6 percent of the theoretical chlorine was present in the filtrate and washings. The apparatus of Examples 2 and 3 was again modified to provide a region of controlled condensation. The upper 13 inch portion of the reactor and part of the transfer line were wrapped with three temperature-controlled electric heat tapes designed to provide a uniform temperature throughout this region of the apparatus. The bottom of the heat-traced region corresponded to the vertical region where the top of the furnace heating elements ended thereby insuring that there would be no condensation regions between the furnace and the temperature-controlled condensation zone. The three heat tapes were kept at 260° C. throughout the duration of the experiment.

The sublimation tube was loaded with a portion of the dried solids produced from the hydrolysis of the lindane-tainted material (8.0 g). Successive layers of quartz wool, quartz chips and quartz wool were placed above the crude TPA as a filtration device. Nitrogen was passed through the steam inlet stem, and the furnace was heated to 220° C. The nitrogen was shut off, and steam preheated to 320° C. was fed through the steam inlet line at a rate of 1.42 g/minute while the furnace continued to heat up.

After the furnace temperature had reached 320° C. the steam feed was continued for 135 minutes. Four white solid samples were isolated from different regions of the condensation train. The solid isolated from the heat-traced portion of the tube (3.02 g) analyzed as 99.41 wt. % TPA with no other detectable impurities. The solid isolated from the heated portion of the transfer line (0.5 g) analyzed as 98.80 wt. % TPA and 0.37 wt. % HETA with no other detectable impurities.

The material isolated from the unheated portion of the transfer line (2.02 g) was wet with water and analyzed as 69.44 wt. % TPA and 2.38 wt. % HETA with the balance being water with no other detectable impurities. After filtration and drying, the solid isolated from the liquid condensate (0.8 g) analyzed as 95.44 wt. % TPA and 4.75 wt. % HETA. None of the four samples contained any detectable lindane (detection limits 20–22 ppb). 10 ppm chlorine was detected in the solid sample isolated from the liquid filtrate, but none was detected in the other three solid samples.

EXAMPLE 5

This example illustrates the application of the process of the invention to a representative sample of mixed polymer waste containing three different types of PET bottle polymer in common usage. In addition to those features demonstrated in previous examples, this example demonstrates the substantial removal of isophthalic acid. The example also demonstrates condensation by mixed liquid/vapor cooling of the TPA-ladened vapor stream.

A representative waste polymer sample was prepared by physically mixing the polymer used in Example 1 (10 wt. %), the green polymer used in Example 3 (50 wt. %) and a sample of PET containing 2.3 mole % copolymerized isophthalic acid (40 wt. %). The mixed polymer sample was hydrolyzed as per Example 1. The dried light green solids isolated from the hydrolysis analyzed as 92.1 wt. % TPA, 5.2 wt. % HETA and 0.41 wt. % isophthalic acid.

The sublimation vessel was constructed of stainless steel, and the upper portion was cylindrical (9 inches diameter × 8.5 inches high) and was flanged at the top. This section tapered down to the bottom cylindrical section (1.5 inches diameter × 4 inches high). The base of the vessel was sealed at the bottom. The total vertical height of the sublimation vessel was 18.5 inches. A stainless steel cap plate with drilled pipe fittings was attached to the top of the vessel flange utilizing a graphite gasket. A 0.25 inch diameter stainless steel steam inlet tube extended from above the stainless steel cap plate through a sealed fitting in the cap plate down to the base of the vessel. A stainless steel heated transfer line (0.5 inch O.D. × 16 inches long) extended from the cap plate to the condensation vessel.

The condensation vessel was fabricated from a stainless steel bucket having bottom diameter = 9 inches, top diameter = 12 inches and vertical distance from top to bottom = 11 inches. The end of the transfer line from the sublimation vessel was attached to the wall of the condensation vessel via a welded fitting to allow the sublimation vapors to enter the condensation vessel at a point 5.5 inches up from the bottom of the vessel, and the design was such to direct the sublimation vapors toward the center of the vessel instead of the vessel walls. During the condensation process a stainless steel cover plate was set on top of the condensation vessel with a layer of quartz wool placed between the plate and the top of the vessel walls to permit pressure equilibration without excessive mixing of process vapors with ambient air.

Cooling of the condensation vessel was performed by contact of the walls of the vessel with the ambient air and by placing solid carbon dioxide on top of the cover plate. During the sublimation/condensation process the average temperature inside the condensation vessel was about 80°–100° C. with large temperature gradients. Liquid water from the condensation of the steam sublimation stream and vapor ensuing from this water were present in sufficient amount to induce condensation of the TPA before the vapors could contact cold wall areas.

The steam inlet line was placed in the sublimation vessel so that it came to within about 0.125 inches of touching the bottom of the vessel. Quartz wool was packed around the bottom of the tube to prevent accidental plugging of the tube with crude TPA. A portion of the product produced by the above described hydrolysis of a representative sample of mixed polymer waste (150.0 g) was placed on top of the quartz wool. Additional quartz wool was placed on top of the crude TPA as a filtration device (extending about half way up into the conical portion of the sublimation vessel). The cap plate and attached transfer line were connected to the sublimation vessel, and sealed to allow vapor to enter only through the steam inlet line and exit only through the transfer line.

The entire system was purged with nitrogen that was fed through the steam inlet line. Nitrogen feed was continued while the sublimation vessel heated up until the temperature of the crude TPA reached 180° C. The nitrogen was then shut off and steam preheated to 320° C. was fed through the steam inlet line at a rate of 6.26 g/minute. The temperature settings during the sublimation process were: for the bottom and tapered portion of the sublimator = 320° C., for the top cylindrical portion of the sublimator = 340°–370° C., for the sublimator cap plate = 370° C., for the transfer line = 380° C. After the temperature of the crude TPA had reached 320° C., the steam feed was continued for 525 minutes.

The white solid product contained in condensation vessel was mostly floating on top of the condensed water, and smaller portions were suspended in the water. No solids were attached to the walls of the vessel. The product was collected in two portions by skimming the surface of the water and by filtering the water. The two portions were combined and dried at 110° C. for 15 hours to yield a white solid (138.8g). The product analyzed as 96.51 wt. % TPA, 1.12 wt. % HETA, no detectable BHET and 0.08 wt. % isophthalic acid, 4 ppm Fe and no detectable Zn, Sb or Ti. The product had the following solution color characteristics: $L^* = 99.31$, $a = 0.52$ and $b^* = 0.90$. The liquid condensate (4162 g)

contained no detectable TPA, HETA, BHET, ethylene glycol, acetaldehyde or other ethylene glycol decomposition products, Zn, Sb, Fe or Ti. The treatments removed 90% of the original IPA. The TPA produced by this example was of polymer grade as demonstrated below in Example 6.

EXAMPLE 6

This example demonstrates that the terephthalic acid produced by the process of the invention can be used as a starting material for the preparation of high quality PET with 25% recycled content which is suitable for use in clear and colored beverage bottles and fiber production as well as other applications. A portion of the sublimed terephthalic acid from PET hydrolysis produced in Example 5 (120.82 g) was mixed with commercial polymer-grade terephthalic acid (PTA, 211.44 g). The ratios were adjusted to result in 25% recycled content (by weight) in the subsequent polymer.

The commercial polymer-grade terephthalic acid was made by oxidizing p-xylene and subsequent purification by conventional procedures. The mixture of terephthalic acids was reacted with ethylene glycol in a molar ratio of 1.75 at a temperature of 255° C. The resulting oligomer was polymerized in the presence of 190 ppm antimony (antimony(III)acetate) at 280° C.

Properties of the poly(ethylene terephthalate) containing 25% recycled content were determined. Properties of poly(ethylene terephthalate) made from virgin terephthalic acid (332.26 g from the same source as the 211.44 g used above) and ethylene glycol in a molar ratio of 1.75 were also determined. Properties of the poly(ethylene terephthalate) with recycled content and of poly(ethylene terephthalate) from 100% commercial content are as follows where the color measurements were performed on granulated solids that passed a 3 mm screen.

| PTA Source | L* | a* | b* | Inherent Viscosity |
|---|---|---|---|---|
| 100% Commercial | 86.335 | −0.46 | 0.89 | 0.61 |
| 36.4% Sublimed from hydrolyzed PET | 85.095 | −0.655 | 2.035 | 0.61 |

The results above indicate that the poly(ethylene terephthalate) made with 36.4% terephthalic acid prepared per this invention from the polymer mixture described in Example 5 has comparable properties to poly(ethylene terephthalate) prepared from 100% virgin terephthalic acid that is commercially available. Similarly good results can be achieved using the sublimed terephthalic acid from PET hydrolysis to provide 1% up to about 100% recycled content in poly(ethylene terephthalate) or any terephthalate-containing homo or copolymer. In addition to homopolymer, this sublimed terephthalic acid from PET hydrolysis can be used to make high quality terephthalate polymers or copolymers, such as but not limited to cyclohexanedimethanol and isophthalic acid modified copolymers. The ethylene glycol recovered in Example 1 can also be used to provide recycled content in poly(ethylene terephthalate), its copolymers or in any polymers containing ethylene glycol.

If the differentially heated condensation zones described in Example 4 were used in the preparation of the purified terephthalic acid used in the polymer, the polymer properties would further approach those of polymer made with 100% virgin purified terephthalic acid.

Unless otherwise specified inherent viscosity is measured in a 60/40 parts by weight solution of phenol-tetrachloroethane at 25° C. and at a concentration of about 0.5 grams of polymer in 100 ml of the solvent.

The L*, b*, a* color characteristics were measured using the CIELAB TM color test. The measurements are in CIELAB TM color units, with a 10° observer angle, the illuminant was D-65, and the test was specular excluded.

We claim:

1. A process for the recovery of ethylene glycol and terephthalic acid from a resin comprised of poly(ethylene terephthalate), wherein said process is a neutral hydrolysis, the process comprising the steps:
   (a) contacting the resin with water at a temperature range of about 200° C. to 280° C. in a reaction vessel at the vapor pressure of water at said temperature range to form a mixture comprised of about 1 to 40 weight percent of the resin;
   (b) cooling the mixture to about 70° C. to 100° C., filtering the solids, washing the solids and then drying the solids at a temperature from about 25° C. to 100° C. to provide a solid portion comprised of terephthalic acid and a liquid portion comprised of ethylene glycol;
   (c) recovering the ethylene glycol from the liquid portion of the mixture by a two-step distillation, wherein in a first step of the two-step distillation the water and low boiling components are removed at about 0.1 to 6 atmospheres pressure and temperatures of about 100° C. to 170° C., and wherein in a second step of the two-step distillation high boiling species are removed at about 1 mm Hg to 10 atmospheres pressure and at a temperature range of about 50° C. to 300° C.;
   (d) recovering the solid terephthalic acid by heating the solid portion above its dew point with a continuous stream of water vapor at a temperature of about 310° C. to 370° C. and a pressure of about 0.1 atmosphere to 1.2 atmosphere to produce a vapor comprised of water and terephthalic acid;
   (e) cooling the vapor containing the terephthalic acid and the water to a temperature below the dew point of the terephthalic acid; and
   (f) collecting solid polymer grade terephthalic acid formed therefrom.

2. The process of claim 1, wherein the poly(ethylene terephthalate) is comprised of at least 50 percent by weight of residues of terephthalic acid.

3. The process of claim 1, wherein the resin is comprised of 90 percent by weight poly(ethylene terephthalate), optionally further comprised of residues of isophthalic acid, diethylene glycol, or 1,4-cyclohexanedimethanol.

4. The process of claim 1, wherein in step (a) the pressure is from about 350 psig to 1500 psig.

5. The process of claim 1, wherein step (a) is conducted in the presence of an inert gas.

6. The process of claim 5, wherein the inert gas is nitrogen.

7. The process of claim 1, wherein in step (c) the low boiling component is acetaldehyde or 2-methyl-1,3-dioxolane.

8. The process of claim 1, wherein in step (c) the high boiling species are selected from the group consisting of diethylene glycol, triethylene glycol, and 1,4-cyclohexanedimethanol.

9. The process of claim 1, wherein in step (d) 3 to 55 moles of the water vapor per mole of the terephthalic acid is used.

10. The process of claim 1, wherein in step (e) the temperature is from about 25° C. to 230° C.

11. The process of claim 1, wherein in step (e) the cooling time is about 0.1 to 100 seconds.

12. The process of claim 1, wherein in step (f) the collection is performed by a cyclone and filter maintained at a temperature in excess of about 110° C.

13. The process of claim 1, wherein recovery of the terephthalic acid is at least 90 percent by weight.

14. The process of claim 1, wherein the process is continuous wherein the reaction vessel is recharged with the resin and steps (a)–(f) are repeated.

15. The process of claim 1, wherein the process is a batch whereby a single sample of resin is processed through steps (a)–(f).

16. A process for the recovery of ethylene glycol from a resin comprised of poly(ethylene terephthalate), wherein said process is a neutral hydrolysis, the process comprising the steps:
  (a) contacting the resin with water at a temperature range of about 200° C. to about 280° C. in a reaction vessel at the vapor pressure of water at said temperature range to form a mixture comprised of about 1 to 40 weight percent of the resin;
  (b) cooling the mixture to about 70° C. to 100° C., filtering the solids, washing the solids and then drying the solids at a temperature of from about 25° C. to about 100° C. to provide a solid portion comprised of terephthalic acid and a liquid portion comprised of ethylene glycol;
  (c) recovering the ethylene glycol from the liquid portion of the mixture by a two-step distillation,
    wherein in a first step of the two-step distillation the water and low boiling components are removed at about 0.1 to 6 atmospheres pressure and temperatures of about 100° C. to 170° C., and
    wherein in a second step of the two-step distillation high boiling species are removed at about 1 mm Hg to 10 atmospheres pressure and at a temperature of about 50° C. to 300° C.;
  (d) recovering the terephthalic acid.

17. The process of claim 16, wherein the resin is comprised of 90 percent by weight poly(ethylene terephthalate).

18. The process of claim 16, wherein in step (a) the pressure is from about 350 psig to about 1500 psig.

19. The process of claim 16, wherein step (a) is conducted under an inert gas.

20. The process of claim 16, wherein the inert gas is nitrogen.

21. The process of claim 16, wherein in step (c) the low boiling contaminant is acetaldehyde or 2-methyl-1,3-dioxolane.

22. The process of claim 16, wherein in step (c) the high boiling species are selected from the group consisting of diethylene glycol, triethylene glycol, and 1,4-cyclohexanedimethanol.

23. The process of claim 16, further comprising polymerizing ethylene glycol with polymer grade terephthalic acid to form recycled poly(ethylene terephthalate).

* * * * *